(12) United States Patent
Xue et al.

(10) Patent No.: US 10,404,802 B2
(45) Date of Patent: Sep. 3, 2019

(54) METHOD AND APPARATUS FOR COORDINATING BODY DEVICES FOR COMMUNICATION

(71) Applicant: Huawei Technologies Co., Ltd., Shenzhen (CN)

(72) Inventors: Xijun Xue, Beijing (CN); Tao Huang, Beijing (CN); Yingtao Li, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 20 days.

(21) Appl. No.: 15/607,080

(22) Filed: May 26, 2017

(65) Prior Publication Data

US 2017/0264693 A1  Sep. 14, 2017

Related U.S. Application Data

(63) Continuation of application No. PCT/CN2015/074924, filed on Mar. 24, 2015.

(30) Foreign Application Priority Data

Nov. 29, 2014 (CN) .......................... 2014 1 0714894

(51) Int. Cl.
*H04M 1/00* (2006.01)
*H04L 29/08* (2006.01)
(Continued)

(52) U.S. Cl.
CPC .......... *H04L 67/125* (2013.01); *G06F 3/0325* (2013.01); *G06F 19/3418* (2013.01);
(Continued)

(58) Field of Classification Search
CPC ...... G06F 19/00; G06F 19/3418; G06F 1/163; G06F 19/3456; G06F 19/3481;
(Continued)

(56) References Cited

U.S. PATENT DOCUMENTS

2006/0140425 A1* 6/2006 Berg ........................ A61B 5/00
381/312
2006/0178567 A1* 8/2006 Goh ..................... A61B 5/0002
600/300

(Continued)

FOREIGN PATENT DOCUMENTS

AU          2013100806 A4    7/2013
CN          102916969 A      2/2013
(Continued)

*Primary Examiner* — Ajibola A Akinyemi
(74) *Attorney, Agent, or Firm* — Leydig, Voit & Mayer, Ltd.

(57) ABSTRACT

The present invention relates to the computer field, and specifically, to a method and an apparatus for coordinating body devices for communication. The method includes: obtaining, by a mobile personal station, an identifier of a body device, and a location parameter and an ambient parameter that are of a user that carries the body device; obtaining, according to the identifier of the body device, a communication mode supported by the body device; obtaining, according to the identifier of the body device, a communication mode supported by the body device; determining, a networking mode of the body device according to the scenario and the communication mode supported by the body device; and establishing, a connection to the body device according to the networking mode.

7 Claims, 10 Drawing Sheets

(51) Int. Cl.
 *H04L 12/28* (2006.01)
 *G06F 3/03* (2006.01)
 *G06F 19/00* (2018.01)
 *G06F 21/32* (2013.01)
 *H04W 72/04* (2009.01)

(52) U.S. Cl.
 CPC ............. *G06F 21/32* (2013.01); *H04L 12/28* (2013.01); *H04W 72/0473* (2013.01)

(58) Field of Classification Search
 CPC .... G06F 19/328; G06F 19/3475; G06F 3/017; G06F 3/165; G06F 17/30864
 USPC ..................................................... 455/552.1
 See application file for complete search history.

(56) References Cited

U.S. PATENT DOCUMENTS

| | | |
|---|---|---|
| 2009/0063187 A1 | 3/2009 | Johnson et al. |
| 2012/0203491 A1 | 8/2012 | Sun et al. |
| 2012/0265026 A1* | 10/2012 | Shenasa ............... A61B 5/0006 600/301 |
| 2014/0292537 A1 | 10/2014 | Huang et al. |
| 2017/0262015 A1 | 9/2017 | Li et al. |

FOREIGN PATENT DOCUMENTS

| | | |
|---|---|---|
| CN | 103281669 A | 9/2013 |
| CN | 103441784 A | 12/2013 |
| CN | 103810254 A | 5/2014 |
| CN | 103957279 A | 7/2014 |
| CN | 105635234 A | 6/2016 |
| JP | 2014017558 A | 1/2014 |
| JP | 2014511189 A | 5/2014 |

\* cited by examiner

A mobile personal station determines a network role of a body device according to a network topology, a network optimization algorithm, and a communication mode supported by the body device, where the network role is a local gateway or a terminal — 301

When the body device is a local gateway, the mobile personal station sends an instruction to a terminal within a preset range, so that the terminal within the preset range establishes a connection to the body device, where the preset range is determined according to a direction and a location that are of the body device — 302

When the body device is a terminal, the mobile personal station sends an instruction to the body device, so that the body device establishes a connection to a gateway closest to the body device, where the network gateway refers to a local gateway or the mobile personal station — 303

FIG. 3

METHOD AND APPARATUS FOR COORDINATING BODY DEVICES FOR COMMUNICATION

CROSS-REFERENCE TO RELATED APPLICATIONS

This application is a continuation of International Application No. PCT/CN2015/074924, filed on Mar. 24, 2015, which claims priority to Chinese Patent Application No. 201410714894.0, filed on Nov. 29, 2014. The disclosures of the aforementioned applications are hereby incorporated by reference in their entireties.

TECHNICAL FIELD

The present invention relates to the communications field, and specifically, to a method and an apparatus for coordinating body devices for communication.

BACKGROUND

With development of sciences and technologies, body devices are emerging endlessly. Body devices mainly include wearable devices and implantable devices. Common wearable devices include devices such as smart bands, smartglasses, and smartwatches. Implantable devices are devices implanted in a human body, for example, devices such as a cardiac pacemaker, a bionic eye, and a sensor. Some of these body devices are used for identity verification, some for illness treatment, some for controlling a remote device, and some for enhancing body performance.

In future, with improvement of living standards, every person is likely to carry hundreds of body devices. For these body devices to implement data transmission, communication is required. However, these body devices do not necessarily have a same communication mode. Therefore, how to coordinate so many body devices to perform communication certainly becomes an important concern of a device carrier.

SUMMARY

Embodiments of the present invention provide a method and an apparatus for coordinating body devices for communication, which can coordinate multiple body devices for communication.

A first aspect of the embodiments of the present invention discloses a method for coordinating body devices for communication, where the method includes:

obtaining, by a mobile personal station, an identifier of a body device, and a location parameter and an ambient parameter that are of a user that carries the body device;

obtaining, by the mobile personal station according to the identifier of the body device, a communication mode supported by the body device;

determining, by the mobile personal station according to the location parameter and the ambient parameter that are of the user, a scenario of the mobile personal station;

determining, by the mobile personal station, a networking mode of the body device according to the scenario and the communication mode supported by the body device; and establishing, by the mobile personal station, a connection to the body device according to the networking mode.

With reference to the first aspect, in a first possible implementation manner of the first aspect, before the determining, by the mobile personal station, a networking mode of the body device according to the scenario and the communication mode supported by the body device, the method further includes:

obtaining, by the mobile personal station, a physiological parameter and a behavior parameter that are of the user, where the determining, by the mobile personal station, a networking mode of the body device according to the scenario and the communication mode supported by the body device specifically includes:

determining, by the mobile personal station, the networking mode of the body device according to the scenario, the communication mode supported by the body device, and the physiological parameter and the behavior parameter that are of the user.

With reference to the first aspect or the first possible implementation manner of the first aspect, in a second possible implementation manner of the first aspect, after the establishing, by the mobile personal station, a connection to the body device according to the networking mode, the method further includes:

determining, by the mobile personal station, a network role of the body device according to a network topology, a network optimization algorithm, and the communication mode supported by the body device, where the network role is a local gateway or a terminal; and when the body device is a local gateway, sending, by the mobile personal station, an instruction to a terminal within a preset range, so that the terminal within the preset range establishes a connection to the body device, where the preset range is determined according to a direction and a location that are of the body device; or when the body device is a terminal, sending, by the mobile personal station, an instruction to the body device, so that the body device establishes a connection to a gateway closest to the body device, where the gateway refers to a local gateway or the mobile personal station, and the mobile personal station determines the gateway closest to the body device according to a location and a direction that are of the body device.

With reference to the second possible implementation manner of the first aspect, in a third possible implementation manner of the first aspect, after the establishing, by the mobile personal station, a connection to the body device according to the networking mode, the method further includes:

monitoring, by the mobile personal station, a working status of the body device by using the established connection;

re-determining, by the mobile personal station, a network role of the body device according to the network topology when the working status of the body device changes; and performing, by the mobile personal station, network optimization according to the network topology and the re-determined network role of the body device.

With reference to the first aspect or the first possible implementation manner of the first aspect or the second possible implementation manner of the first aspect or the third possible implementation manner of the first aspect, in a fourth possible implementation manner of the first aspect, before the establishing, by the mobile personal station, a connection to the body device according to the networking mode, the method further includes:

receiving, by the mobile personal station, a connection request sent by the body device, where the connection request includes a most power-saving connection mode supported by the body device; and establishing, by the mobile personal station, a connection according to the most power-saving connection mode; where the establishing, by the mobile personal station, a connection to the body device according to the networking mode specifically includes:

re-establishing, by the mobile personal station, a connection to the body device according to the networking mode when the networking mode is different from the most power-saving connection mode.

A second aspect of the embodiments of the present invention discloses an apparatus for coordinating body devices for communication, where the apparatus includes:

an obtaining unit, configured to obtain an identifier of a body device, and a location parameter and an ambient parameter that are of a user that carries the body device, where the obtaining unit is further configured to obtain, according to the identifier of the body device, a communication mode supported by the body device;

a first determining unit, configured to determine, according to the location parameter and the ambient parameter that are of the user, a scenario of the mobile personal station, where the first determining unit is further configured to determine a networking mode of the body device according to the scenario and the communication mode supported by the body device; and a first connection unit, configured to establish a connection to the body device according to the networking mode.

With reference to the second aspect, in a first possible implementation manner of the second aspect, the obtaining unit is further configured to obtain a physiological parameter and a behavior parameter that are of the user; and the first determining unit is specifically configured to determine the networking mode of the body device according to the scenario, the communication mode supported by the body device, and the physiological parameter and the behavior parameter that are of the user.

With reference to the second aspect or the first possible implementation manner of the second aspect, in a second possible implementation manner of the second aspect, after the mobile personal station establishes the connection to the body device according to the networking mode, the apparatus further includes a second determining unit and a sending unit, where the second determining unit is configured to determine a network role of the body device according to a network topology, a network optimization algorithm, and the communication mode supported by the body device, where the network role is a local gateway or a terminal;

the sending unit is configured to: when the body device is a local gateway, the mobile personal station sends an instruction to a terminal within a preset range, so that the terminal within the preset range establishes a connection to the body device, where the preset range is determined according to a direction and a location that are of the body device; and the sending unit is further configured to: when the body device is a terminal, send an instruction to the body device, so that the body device establishes a connection to a gateway closest to the body device, where the gateway refers to a local gateway or the mobile personal station, and the mobile personal station determines the gateway closest to the body device according to the location and the direction that are of the body device.

With reference to the second possible implementation manner of the second aspect, in a third possible implementation manner of the second aspect, the apparatus further includes a monitoring unit, a third determining unit, and a network optimization unit, where the monitoring unit is configured to monitor a working status of the body device by using the connection established by the first connection unit;

the third determining unit is configured to re-determine a network role of the body device according to the network topology when the working status of the body device changes; and the network optimization unit is configured to perform network optimization according to the network topology and the re-determined network role of the body device.

With reference to the second aspect or the first possible implementation manner of the second aspect or the second possible implementation manner of the second aspect or the third possible implementation manner of the second aspect, in a fourth possible implementation manner of the second aspect, the apparatus further includes a receiving unit and a second connection unit, where the receiving unit is configured to receive a connection request sent by the body device, where the connection request includes a most power-saving connection mode supported by the body device;

the second connection unit is configured to establish a connection according to the most power-saving connection mode; and the first connection unit is configured to re-establish a connection to the body device according to the networking mode when the networking mode is different from the most power-saving connection mode.

It can be learned from the foregoing that, by using the method and the apparatus for coordinating body devices for communication provided in the embodiments of the present invention, a mobile personal station obtains an identifier of a body device, and a location parameter and an ambient parameter that are of a user that carries the body device; the mobile personal station obtains, according to the identifier of the body device, a communication mode supported by the body device; the mobile personal station determines, according to the location parameter and the ambient parameter that are of the user, a scenario of the mobile personal station; the mobile personal station determines a networking mode of the body device according to the scenario and the communication mode supported by the body device; and the mobile personal station establishes a connection to the body device according to the networking mode. A user's scenario and the communication mode supported by the body device are used to determine the networking mode of the body device, which implements communication coordination between body devices and improves user experience.

BRIEF DESCRIPTION OF DRAWINGS

To describe the technical solutions in the embodiments of the present invention more clearly, the following briefly describes the accompanying drawings required for describing the embodiments. Apparently, the accompanying drawings in the following description show merely some embodiments of the present invention, and a person of ordinary skill in the art may still derive other drawings from these accompanying drawings without creative efforts.

FIG. 3 is a flowchart of a method for coordinating body devices for communication according to another embodiment of the present invention;

DESCRIPTION OF EMBODIMENTS

The following clearly describes the technical solutions in the embodiments of the present invention with reference to the accompanying drawings in the embodiments of the present invention. Apparently, the described embodiments are merely some but not all of the embodiments of the present invention. All other embodiments obtained by a person of ordinary skill in the art based on the embodiments of the present invention without creative efforts shall fall within the protection scope of the present invention.

As is for innovations and changes brought by automobiles, computers, the Internet, and smartphones, it is difficult to figure out a specific time taken from emergence to maturity and then to popular use of body devices by using simple production and sales volumes. However, body devices are obviously developing more quickly and are sure to bring extraordinary and incomparable impact on the future.

Body devices mainly include wearable devices and implantable devices. Common wearable devices include devices such as smart bands, smartglasses, and smartwatches. Implantable devices are devices implanted in a human body, for example, devices such as a cardiac pacemaker, a bionic eye, and a sensor. Some of these body devices are used for identity verification, some for illness treatment, some for controlling a remote device, and some for enhancing body performance.

In the long run, with maturity and popularization of body devices, every person is likely to carry hundreds of body devices. With such a quantity of body devices, how to coordinate so many body devices for communication certainly becomes an important concern of a device carrier. In view of this, the embodiments of the present invention provide a method and an apparatus for coordinating body devices for communication, which can coordinate multiple body devices for communication, thereby resolving the foregoing concern.

Figure 1:
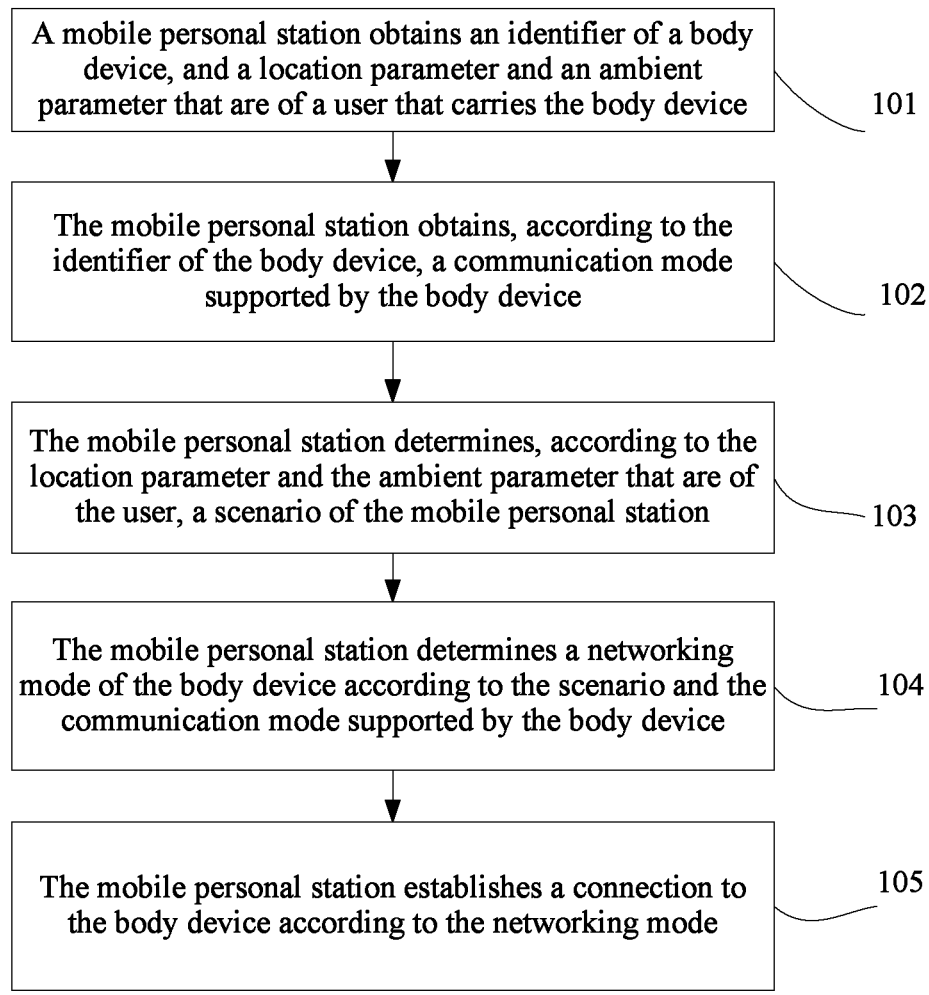
FIG. 1 is a flowchart of a method for coordinating body devices for communication according to an embodiment of the present invention.

As shown in FIG. 1, FIG. 1 shows a method for coordinating body devices for communication in an embodiment of the present invention. The method specifically includes step 101 to step 104.

101: A mobile personal station obtains an identifier of a body device, and a location parameter and an ambient parameter that are of a user that carries the body device.

The mobile personal station (MPS, Mobile personal station) is an apparatus that coordinates body devices for communication. The mobile personal station may be considered as one type of body device. The mobile personal station is small and portable for a user to carry. For example, the user may wear it on the wrist, tie it around the waist, or place it in a bag. There are many manners to attach the mobile personal station to a human body, which are not listed one by one herein.

The identifier of the body device is used to uniquely identify the body device. For example, the identifier of the body device may be a factory-assigned serial number of the body device.

The identifier of the body device may be entered by the user to the mobile personal station.

The body device sends a connection request to the mobile personal station. The connection request includes the identifier of the body device. The mobile personal station obtains the identifier of the body device from the connection request.

The location parameter of the user refers to parameters such as a latitude, a longitude, and an altitude that are of a location of the user.

The ambient parameter of the user refers to parameters such as a temperature, a humidity, an air quality, a carbon dioxide concentration, an ultraviolet ray strength, and a wind scale that are at the location of the user.

The mobile personal station may obtain the location parameter of the user by using a location sensor or a network map. The location sensor may be a body device, or a function of the mobile personal station itself.

The mobile personal station may obtain, by using an ambient sensor or a network, the ambient parameter of the location of the user. The ambient sensor may be a body device, or a function of the mobile personal station itself.

All parameters of the body device can be obtained by using the identifier of the body device, such as the identifier, a name, a category, a type, a battery power status, and a supported communication mode that are of the body device. The identifier may be a serial number. The name may be a name specified by a manufacturer or may be a name specified by the user.

The mobile personal station is a device configured to assist the user in coordinating a large quantity of body devices for communication. The mobile personal station automatically determines a communication mode of the body device, and maintains and optimizes network operation.

102: The mobile personal station obtains, according to the identifier of the body device, a communication mode supported by the body device.

The mobile personal station may traverse a body device list built in the mobile personal station to obtain the communication mode supported by the body device. The body device list includes some parameters or all parameters of body devices. The body device list may be constructed according to brands of the body devices or may be constructed according to types of the body devices. A specific construction manner of the body device list is not limited herein. The mobile personal station traverses the body device list according to the identifier of the body device to obtain information about the body device from the body device list. Common information about a body device includes: a communication mode, a communication priority, a battery power status, a device category, a device type, and the like that are of the body device.

The mobile personal station may use the identifier of the body device to search a network for the communication mode supported by the body device.

Common communication modes include Bluetooth connection, Wi-Fi (Wireless Fidelity, Wireless Fidelity) connection, infrared ray connection, NFC (Near Field Communication, Near Field Communication) connection, terahertz connection, and the like.

103: The mobile personal station determines, according to the location parameter and the ambient parameter that are of the user, a scenario of the mobile personal station.

The location parameter of the user includes parameters such as a latitude, a longitude, and an altitude that are of a location of the user. A city and a climate at the location of the user may be determined according to the latitude, the longitude, and the altitude of the location of the user.

The ambient parameter of the user includes parameters such as a temperature, a humidity, a wind scale, an ultraviolet ray strength, a carbon dioxide concentration, and an oxygen concentration that are at the location of the user. A living environment in which the user is in may be determined according to the parameters such as the temperature, the humidity, and the wind scale that are at the location of the user.

The mobile personal station enters the location parameter and the ambient parameter that are of the user into a scenario model for computation. The scenario model includes many scenarios, and each scenario has a corresponding parameter range. After the location parameter and the ambient parameter that are of the user are entered into the scenario model, the mobile personal station obtains, according to the location parameter and the ambient parameter that are of the user, an appropriate scenario by means of matching. For example, if the humidity is quite high, the oxygen concentration is quite low, and the user is in a seaside city, A user's scenario may be swimming in a swimming pool or in a sea.

The scenario model may be preset or may be obtained by training using historical data.

104: The mobile personal station determines a networking mode of the body device according to the scenario and the communication mode supported by the body device.

The networking mode means that which communication mode is used to connect to the mobile personal station. For example, the scenario is a swimming pool, and the communication mode supported by the body device includes Wi-Fi and Bluetooth. In this case, the user is probably not using the body device; and the mobile personal station may use Bluetooth to connect to the body device because Bluetooth is more power-saving compared with Wi-Fi.

The mobile personal station functions like a gateway. The body device may be connected to the Internet by using the mobile personal station.

105: The mobile personal station establishes a connection to the body device according to the networking mode.

There are many modes for the mobile personal station to establish a connection to the body device according to the networking mode, which include but are not limited to the following two:

First mode: The mobile personal station sends a connection request to the body device, where the connection request includes the networking mode, so that the body device establishes the connection to the mobile personal station according to the networking mode.

Second mode: The mobile personal station sends indication information to the body device, where the indication information includes the networking mode, so that the body device sends a connection request to the mobile personal station according to the networking mode. The mobile personal station establishes the connection according to the connection request.

It can be learned from the foregoing that, by using the method for coordinating body devices for communication provided in this embodiment of the present invention, a mobile personal station obtains an identifier of a body device, and a location parameter and an ambient parameter that are of a user; the mobile personal station obtains, according to the identifier of the body device, a communication mode supported by the body device; the mobile personal station determines, according to the location parameter and the ambient parameter that are of the user, a scenario of the mobile personal station; the mobile personal station determines a networking mode of the body device according to the scenario and the communication mode supported by the body device; and the mobile personal station establishes a connection to the body device according to the networking mode. A user's scenario and the communication mode supported by the body device are used to determine the networking mode of the body device, which implements communication coordination between body devices and improves user experience.

Figure 2:
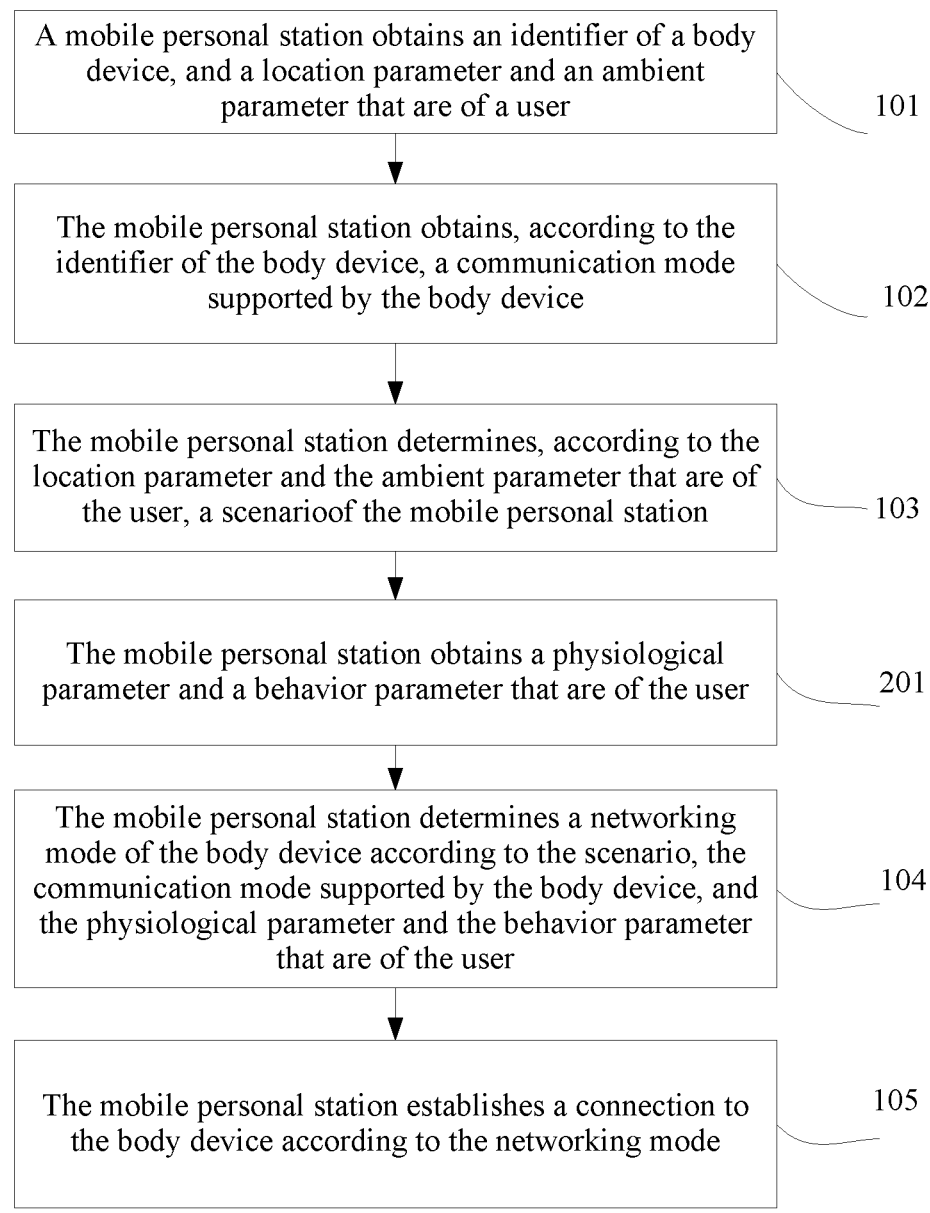
FIG. 2 is a flowchart of a method for coordinating body devices for communication according to another embodiment of the present invention.

Optionally, as shown in FIG. 2, on the basis of the foregoing embodiment, in another embodiment of the present invention, before step 104, the following step is further included:

Step 201: The mobile personal station obtains a physiological parameter and a behavior parameter that are of the user.

The physiological parameter of the user includes parameters such as a blood pressure, and a heart rate.

The behavior parameter of the user includes parameters such as a get-up time of the user, a go-to-bed time of the user, in-bed duration of the user, an Internet-surfing start time of the user, and an Internet-surfing time period of the user.

Step 104 that the mobile personal station determines a networking mode of the body device according to the scenario and the communication mode supported by the body device specifically includes:

the mobile personal station determines the networking mode of the body device according to the scenario, the communication mode supported by the body device, and the physiological parameter and the behavior parameter that are of the user.

The networking mode means that which communication mode is used to connect to the mobile personal station. For example, the scenario is that the user is in bed at home, and communication modes supported by the body device include Wi-Fi and Bluetooth. In this case, the user is probably not using the body device; and the mobile personal station may use Bluetooth to connect to the body device because Bluetooth is more power-saving compared with Wi-Fi. For example, the scenario is that the user is surfing the Internet, and communication modes supported by the body device include Wi-Fi and Bluetooth. In this case, the user probably requires a high network speed; and the mobile personal station may use Wi-Fi to connect to the body device because Wi-Fi has a higher transmission speed compared with Bluetooth.

It can be learned from the foregoing that, by using the method for coordinating body devices for communication provided in this embodiment of the present invention, the mobile personal station obtains a physiological parameter and a behavior parameter that are of the user; and the mobile personal station determines a networking mode of the body device according to the scenario, the communication mode supported by the body device, and the physiological parameter and the behavior parameter that are of the user. In this way, the networking mode of the body device can be determined more accurately, and using the networking mode also makes it more convenient for the body device to communicate with the mobile personal station, which improves user experience.

Optionally, as shown in FIG. 3, on the basis of the foregoing embodiment, in another embodiment of the present invention, after step 105, the following steps are further included.

301: The mobile personal station determines a network role of the body device according to a network topology, a network optimization algorithm, and the communication mode supported by the body device, where the network role is a local gateway or a terminal.

The network optimization algorithm may use a layered routing protocol or a plane-based routing protocol. There are many specific algorithms, but they all need to possess the following characteristics: fast convergence; provision of loopless routing; avoidance of infinite calculation; low control management overheads; and support for unidirectional channels. The layered routing protocol or the plane-based routing protocol needs to adapt to three ever-changing basic characteristics of a network: an overall density of mobile nodes; a node-to-node topology; and an operational mode of the network.

Body devices are tending to get miniature. Therefore, body devices for people in the future are to be diversified in size. There will also be varied radio frequency bands used in short-distance communication. A micro-sized or nanometer-sized body device can use a frequency spectrum at only a terahertz waveband to perform wireless communication with another body device. However, restricted by power consumption, the micro-sized or nanometer-sized body device is to have a quite limited transmission distance. Therefore, multi-hop wireless transmission is to become a necessary choice. Future body devices and communication are to present an ecology with body devices diversified in size, co-existence of multi-hop and single-hop networks, different spectra used in communication, and co-existence of wired communication and wireless communication, where in wired communication, a human body is used as a conductor for communication.

On a multi-hop network, a local gateway is required. Some body devices support quite a few communication modes and have a relatively strong computing capability. These body devices may be determined to be local gateways according to the network optimization algorithm and the network topology.

302: When the body device is a local gateway, the mobile personal station sends an instruction to a terminal within a preset range, so that the terminal within the preset range establishes a connection to the body device, where the preset range is determined according to a direction and a location that are of the body device.

The mobile personal station can sense the direction and the location of the body device based on strength of a signal, and determine a signal coverage range of the body device according to the direction and the location of the body device. This signal coverage range is the preset range.

A structure of a human body is definite. Therefore, nodes on a wireless multi-hop network can be distributed according to only the structure of the human body. For example, if the MPS is located in the waist of the human body, nodes of multiple hops that can directly communicate with the MPS can be located only within a preset radius range with the MPS as a central point.

303: When the body device is a terminal, the mobile personal station sends an instruction to the body device, so that the body device establishes a connection to a gateway closest to the body device, where the network gateway refers to a local gateway or the mobile personal station, and the mobile personal station determines the gateway closest to the body device according to a location and a direction of the body device.

It can be learned from the foregoing that, by using the method for coordinating body devices for communication provided in this embodiment of the present invention, the mobile personal station determines a network role of the body device according to a network topology, a network optimization algorithm, and the communication mode supported by the body device, where the network role includes a local gateway and a terminal; when the body device is a local gateway, the mobile personal station sends an instruction to a terminal within a preset range, so that the terminal within the preset range establishes a connection to the body device, where the preset range is determined according to a direction and a location that are of the body device; or when the body device is a terminal, the mobile personal station sends an instruction to the body device, so that the body device establishes a connection to a gateway closest to the body device, where the gateway refers to a local gateway or the mobile personal station, and the mobile personal station determines the gateway closest to the body device according to a location and a direction that are of the body device. In this way, the network connection is established according to the network role of the body device, thereby implementing communication coordination between body devices.

Figure 4:
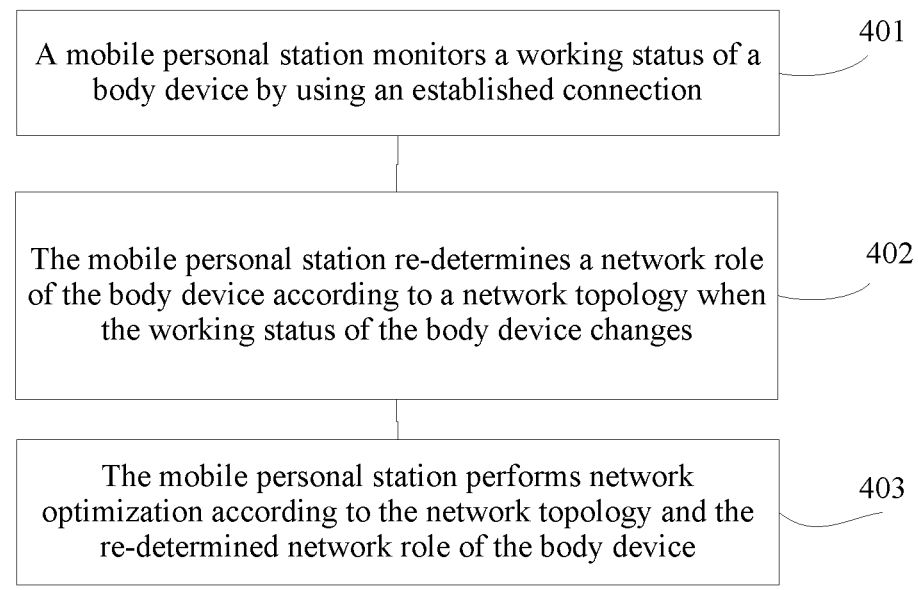
FIG. 4 is a flowchart of a method for coordinating body devices for communication according to another embodiment of the present invention.

Optionally, as shown in FIG. 4, on the basis of the foregoing embodiment, in another embodiment of the present invention, after step 105, the following steps are further included.

401: The mobile personal station monitors a working status of the body device by using the established connection.

The working status includes states such as being dormant, power-off, overloaded, under-loaded, and normal-loaded.

402: The mobile personal station re-determines a network role of the body device according to the network topology when the working status of the body device changes.

Figure 5:
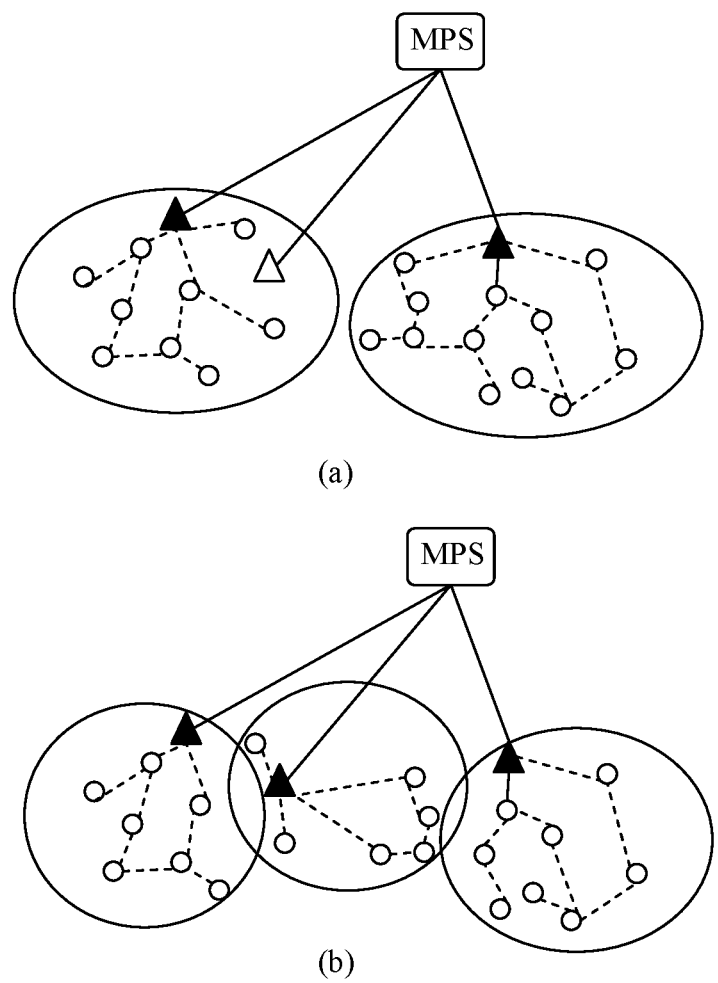
FIG. 5 is a schematic diagram of network optimization according to another embodiment of the present invention.

Because body devices have different computing capabilities, a layered routing method may be used to construct a network. Layered routing requires clustering of nodes on the network, and each cluster forms a routing subnet. According to a behavior habit of the user and A user's scenario, when a body device is not in use, the body device is made dormant with best effort to save power. Therefore, the topology of the body network is changing constantly. The MPS can manage all the body devices. Therefore, the MPS may optimize and adjust the clustering according to working statuses of all the body devices. For example, in FIG. 5, there is a body device that is represented by a triangle. The body device is provided with both a Bluetooth interface and a terahertz interface. The body device is in a dormant state. Currently, an entire multi-hop network is divided into two clusters. When the dormant triangle-shaped device is waken up, the MPS may determine, according to current load and other statuses of two cluster heads, whether a third cluster needs to be set. If a third cluster is needed, the device is set as a cluster head of the third cluster, and some nodes are allotted from the other two clusters to be managed by the device.

403: The mobile personal station performs network optimization according to the network topology and the re-determined network role of the body device.

It can be learned from the foregoing that, by using the method for coordinating body devices for communication provided in this embodiment of the present invention, the mobile personal station monitors a working status of the body device; the mobile personal station re-determines a network role of the body device according to the network topology when the working status of the body device changes; and the mobile personal station performs network optimization according to the network topology and the re-determined network role of the body device. In this way, network optimization is performed according to the status of the body device, which can improve efficiency of coordinating body devices for communication.

Figure 6:
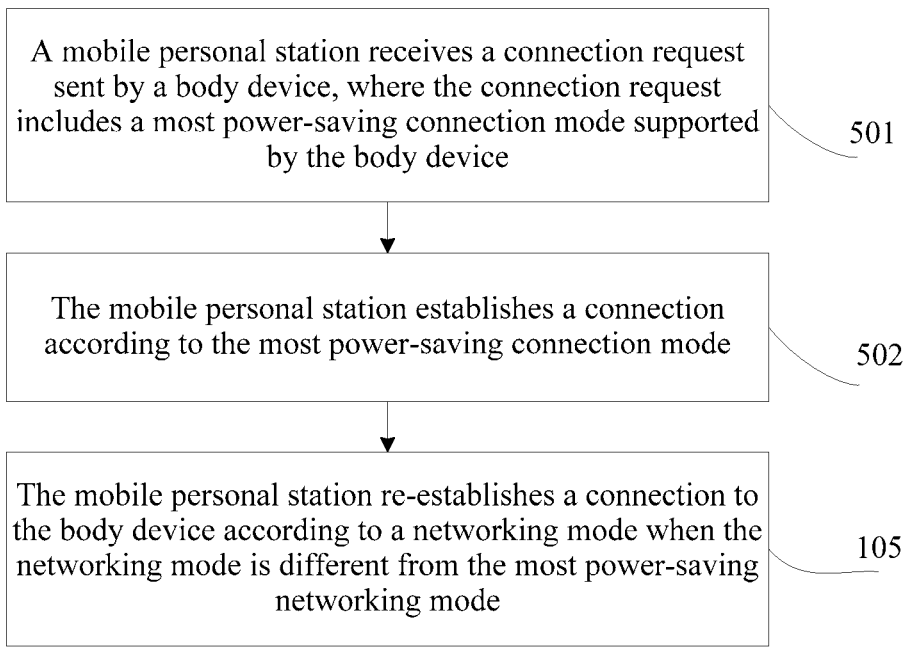
FIG. 6 is a flowchart of a method for coordinating body devices for communication according to another embodiment of the present invention.

Optionally, as shown in FIG. 6, on the basis of the foregoing embodiment, in another embodiment of the present invention, before step 105, the following steps are further included:

501: The mobile personal station receives a connection request sent by the body device, where the connection request includes a most power-saving connection mode supported by the body device.

502: The mobile personal station establishes a connection according to the most power-saving connection mode.

Step 105 that the mobile personal station establishes a connection to the body device according to the networking mode specifically includes:

the mobile personal station re-establishes a connection to the body device according to the networking mode when the networking mode is different from the most power-saving connection mode.

It can be learned from the foregoing that, by using the method for coordinating body devices for communication provided in this embodiment of the present invention, the mobile personal station receives a connection request sent by the body device, where the connection request includes a most power-saving connection mode supported by the body device; the mobile personal station establishes a connection according to the most power-saving connection mode; and the mobile personal station re-establishes a connection to the body device according to the networking mode when the networking mode is different from the most power-saving connection mode. Whether the current connection mode suits the current scenario is determined according to the networking mode; and if the current connection mode does not suit the current scenario, a connection is re-established according to the networking mode. This can improve efficiency of coordinating body devices for communication and improve user experience.

Figure 7:
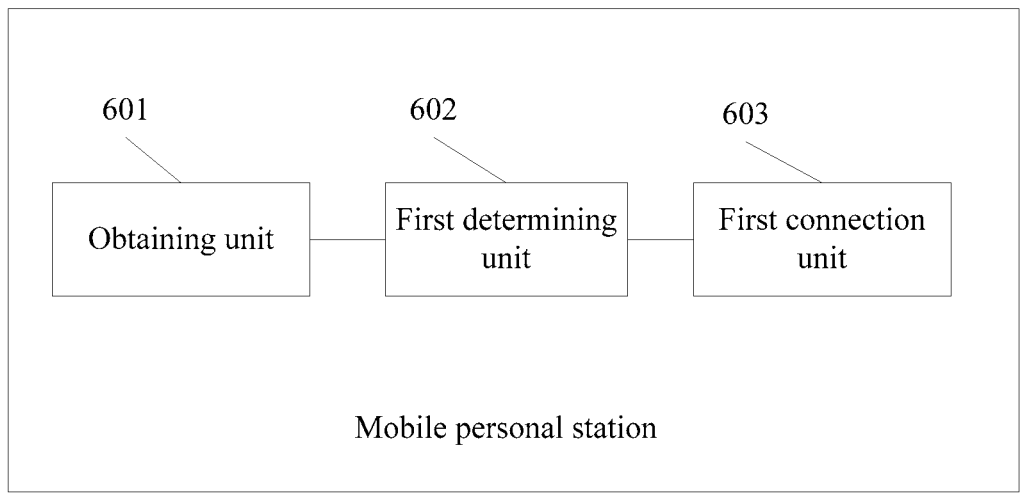
FIG. 7 is a structural diagram of an apparatus for coordinating body devices for communication according to an embodiment of the present invention.

As shown in FIG. 7, FIG. 7 shows an apparatus for coordinating body devices for communication, that is, a mobile personal station, in an embodiment of the present invention. The mobile personal station is an apparatus that coordinates body devices for communication. The mobile personal station may be considered as one type of body device. The mobile personal station is small and portable for a user to carry. For example, the user may wear it on the wrist, tie it around the waist, or place it in a bag. There are many manners to attach the mobile personal station to a human body, which are not listed one by one herein. The mobile personal station 60 is configured to execute the method for coordinating body devices for communication described in the foregoing embodiments. The mobile personal station 60 includes an obtaining unit 601, a first determining unit 602, and a first connection unit 603.

The obtaining unit 601 is configured to obtain an identifier of the body device, and a location parameter and an ambient parameter that are of a user that carries the body device.

The identifier of the body device is used to uniquely identify the body device. For example, the identifier of the body device may be a factory-assigned serial number of the body device.

The location parameter of the user refers to parameters such as a latitude, a longitude, and an altitude that are of a location of the user.

The ambient parameter of the user refers to parameters such as a temperature, a humidity, an air quality, a carbon dioxide concentration, an ultraviolet ray strength, and a wind scale that are at the location of the user.

The obtaining unit 601 is further configured to obtain, according to the identifier of the body device, a communication mode supported by the body device.

Common communication modes include Bluetooth connection, Wi-Fi connection, infrared ray connection, NFC connection, terahertz connection, and the like.

The first determining unit 602 is configured to determine, according to the location parameter and the ambient parameter that are of the user, a scenario of the mobile personal station.

Common scenarios include a scenario in which the user is in bed, a scenario in which the user is at work, a scenario in which the user is surfing the Internet for entertainment, a scenario in which the user is outdoor doing sports, and the like.

The first determining unit 602 is further configured to determine a networking mode of the body device according to the scenario and the communication mode supported by the body device.

Common networking modes include Wi-Fi, Bluetooth, terahertz, and the like.

The first connection unit 603 is configured to establish a connection to the body device according to the networking mode.

It can be learned from the foregoing that, by using the apparatus for coordinating body devices for communication provided in this embodiment of the present invention, a mobile personal station obtains an identifier of a body device, and a location parameter and an ambient parameter that are of a user; the mobile personal station obtains, according to the identifier of the body device, a communication mode supported by the body device; the mobile personal station determines, according to the location parameter and the ambient parameter that are of the user, a scenario of the mobile personal station; the mobile personal station determines a networking mode of the body device according to the scenario and the communication mode supported by the body device; and the mobile personal station establishes a connection to the body device according to the networking mode. A user's scenario and the communication mode supported by the body device are used to determine the networking mode of the body device, which implements communication coordination between body devices and improves user experience.

Optionally, based on the foregoing apparatus:

the obtaining unit 601 is further configured to obtain a physiological parameter and a behavior parameter that are of the user.

The physiological parameter of the user includes parameters such as a blood pressure, and a heart rate.

The behavior parameter of the user includes parameters such as a get-up time of the user, a go-to-bed time of the user, in-bed duration of the user, an Internet-surfing start time of the user, and an Internet-surfing time period of the user.

The first determining unit 602 is specifically configured to determine the networking mode of the body device according to the scenario, the communication mode supported by the body device, and the physiological parameter and the behavior parameter that are of the user.

It can be learned from the foregoing that, by using the apparatus for coordinating body devices for communication provided in this embodiment of the present invention, the mobile personal station obtains a physiological parameter and a behavior parameter that are of the user; and the mobile personal station determines a networking mode of the body device according to the scenario, the communication mode supported by the body device, and the physiological parameter and the behavior parameter that are of the user. In this way, the networking mode of the body device can be determined more accurately, and using the networking mode also makes it more convenient for the body device to communicate with the mobile personal station, which improves user experience.

Figure 8:
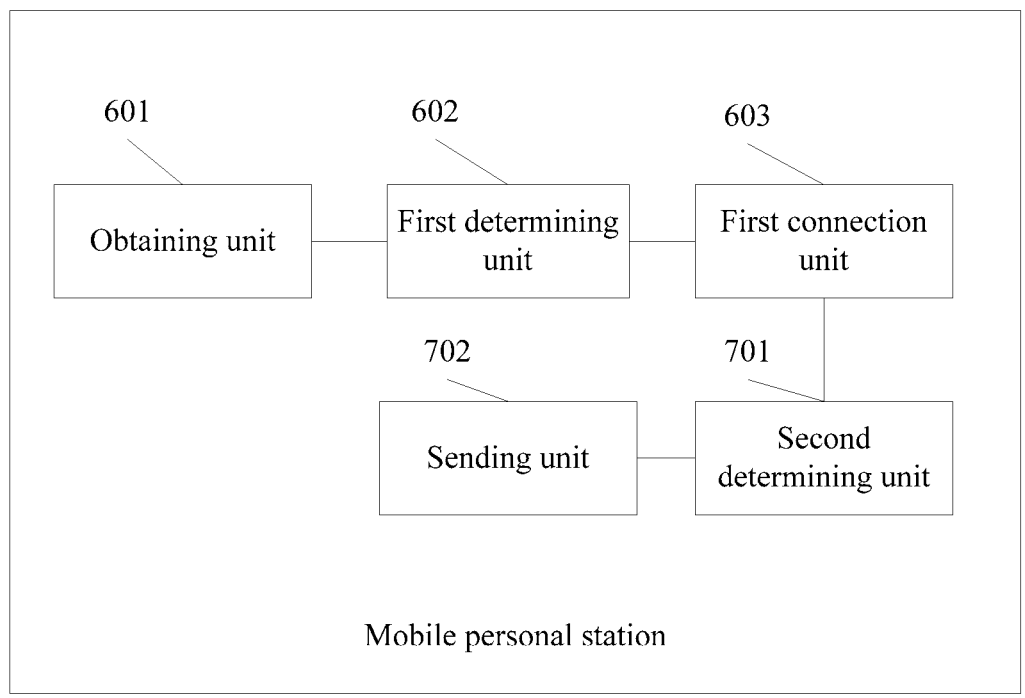
FIG. 8 is a structural diagram of an apparatus for coordinating body devices for communication according to another embodiment of the present invention.

Optionally, as shown in FIG. 8, based on the foregoing apparatus, the apparatus further includes a second determining unit 701 and a sending unit 702.

The second determining unit 701 is configured to determine a network role of the body device according to a network topology, a network optimization algorithm, and the communication mode supported by the body device, where the network role is a local gateway or a terminal.

The second determining unit 701 is connected to the first connection unit 603.

The sending unit 702 is configured to: when the body device is a local gateway, the mobile personal station sends an instruction to a terminal within a preset range, so that the terminal within the preset range establishes a connection to the body device, where the preset range is determined according to a direction and a location that are of the body device.

The sending unit 702 is further configured to: when the body device is a terminal, send an instruction to the body device, so that the body device establishes a connection to a gateway closest to the body device, where the gateway refers to a local gateway or the mobile personal station, and the mobile personal station determines the gateway closest to the body device according to the location and the direction that are of the body device.

It can be learned from the foregoing that, by using the apparatus for coordinating body devices for communication provided in this embodiment of the present invention, the mobile personal station determines a network role of the body device according to a network topology, a network optimization algorithm, and the communication mode supported by the body device, where the network role includes a local gateway and a terminal; when the body device is a local gateway, the mobile personal station sends an instruction to a terminal within a preset range, so that the terminal within the preset range establishes a connection to the body device, where the preset range is determined according to a direction and a location that are of the body device, or when the body device is a terminal, the mobile personal station sends an instruction to the body device, so that the body device establishes a connection to a gateway closest to the body device, where the gateway refers to a local gateway or the mobile personal station, and the mobile personal station determines the gateway closest to the body device according to a location and a direction that are of the body device. In this way, the network connection is established according to the network role of the body device, thereby implementing communication coordination between body devices.

Figure 9:
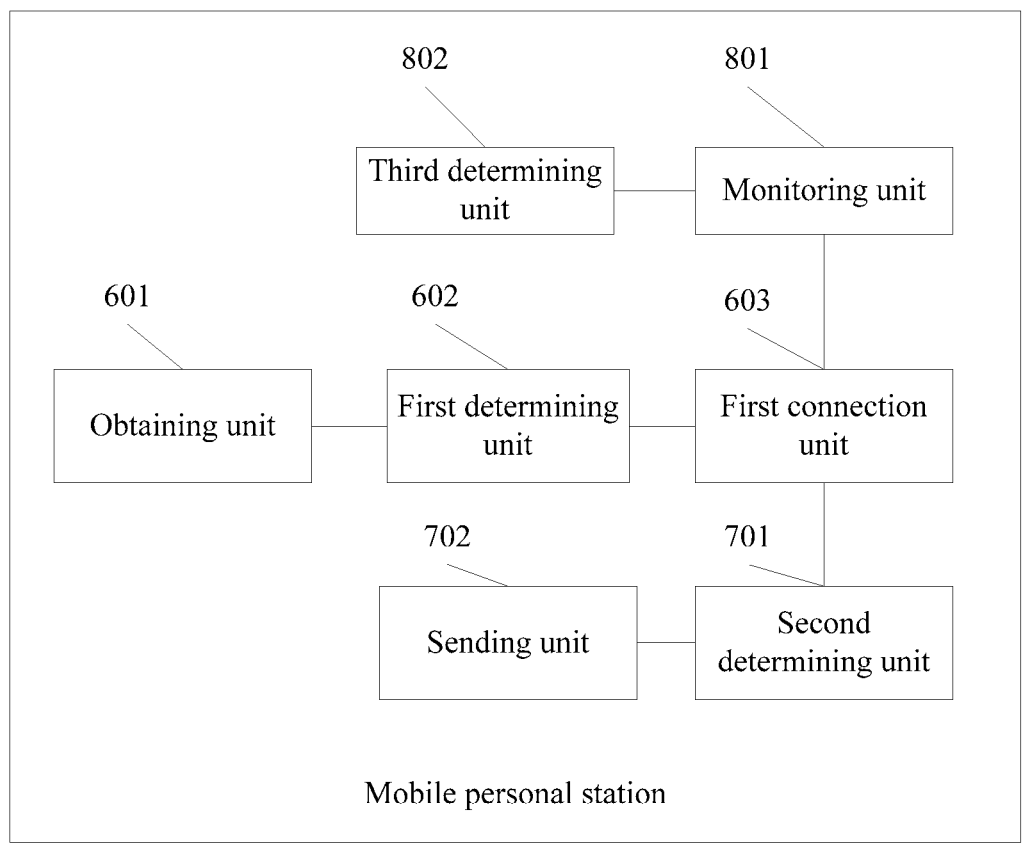
FIG. 9 is a structural diagram of an apparatus for coordinating body devices for communication according to another embodiment of the present invention.

Optionally, as shown in FIG. 9, based on the foregoing apparatus, the apparatus further includes a monitoring unit 801, a third determining unit 802, and a network optimization unit.

The monitoring unit 801 is configured to monitor a working status of the body device by using the connection established by the first connection unit 603.

The third determining unit 802 is configured to re-determine a network role of the body device according to the network topology when the working status of the body device changes.

The network optimization unit 803 is configured to perform network optimization according to the network topology and the re-determined network role of the body device.

It can be learned from the foregoing that, by using the apparatus for coordinating body devices for communication provided in this embodiment of the present invention, the mobile personal station monitors a working status of the body device; the mobile personal station re-determines a network role of the body device according to the network topology when the working status of the body device changes; and the mobile personal station performs network optimization according to the network topology and the re-determined network role of the body device. In this way, network optimization is performed according to the status of the body device, which can improve efficiency of coordinating body devices for communication.

Figure 10:
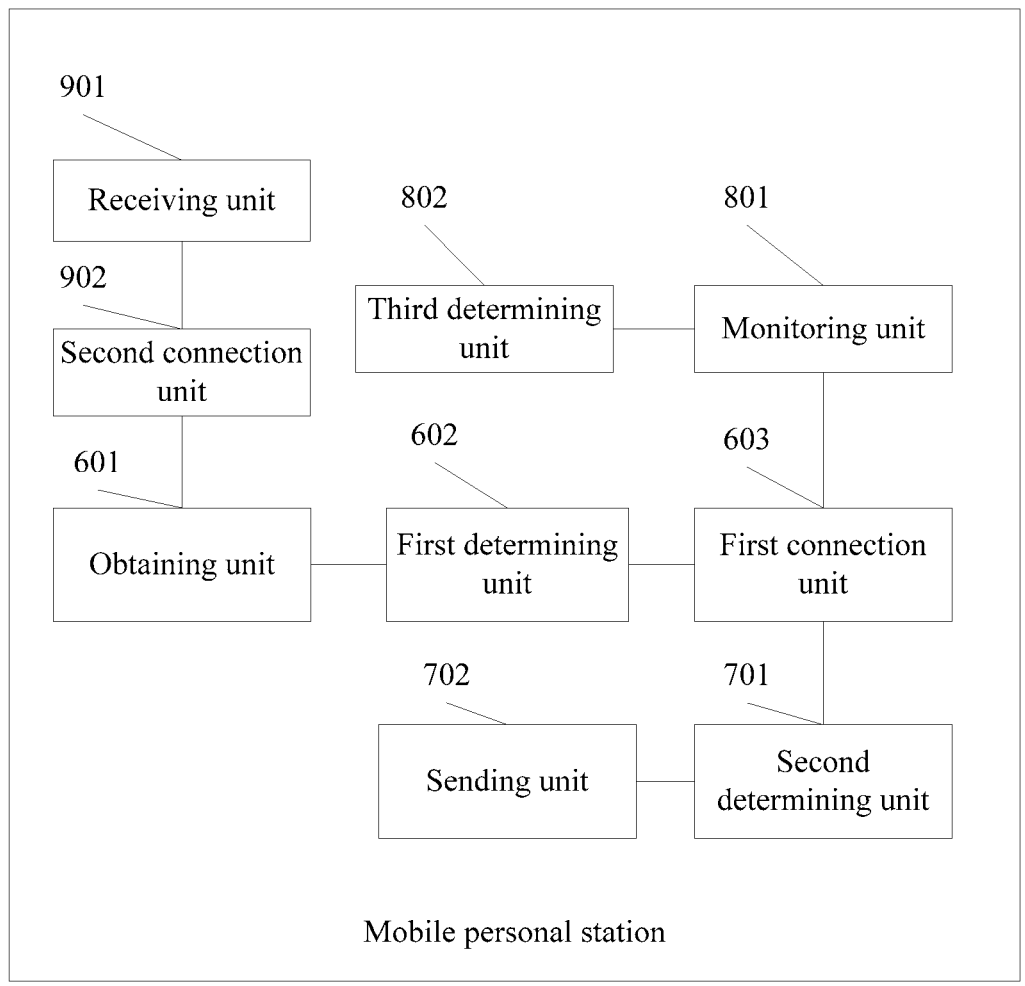
FIG. 10 is a structural diagram of an apparatus for coordinating body devices for communication according to another embodiment of the present invention.

Optionally, as shown in FIG. 10, based on the foregoing apparatus, the apparatus further includes a receiving unit 901 and a second connection unit 902.

The receiving unit 901 is configured to receive a connection request sent by the body device, where the connection request includes a most power-saving connection mode supported by the body device.

The second connection unit 902 is configured to establish a connection according to the most power-saving connection mode.

The first connection unit 603 is configured to re-establish a connection to the body device according to the networking mode when the networking mode is different from the most power-saving connection mode.

It can be learned from the foregoing that, by using the apparatus for coordinating body devices for communication provided in this embodiment of the present invention, the mobile personal station receives a connection request sent by the body device, where the connection request includes a most power-saving connection mode supported by the body device; the mobile personal station establishes a connection according to the most power-saving connection mode; and the mobile personal station re-establishes a connection to the body device according to the networking mode when the networking mode is different from the most power-saving connection mode. Whether the current connection mode suits the current scenario is determined according to the networking mode; and if the current connection mode does not suit the current scenario, a connection is re-established according to the networking mode. This can improve efficiency of coordinating body devices for communication and improve user experience.

Figure 11:
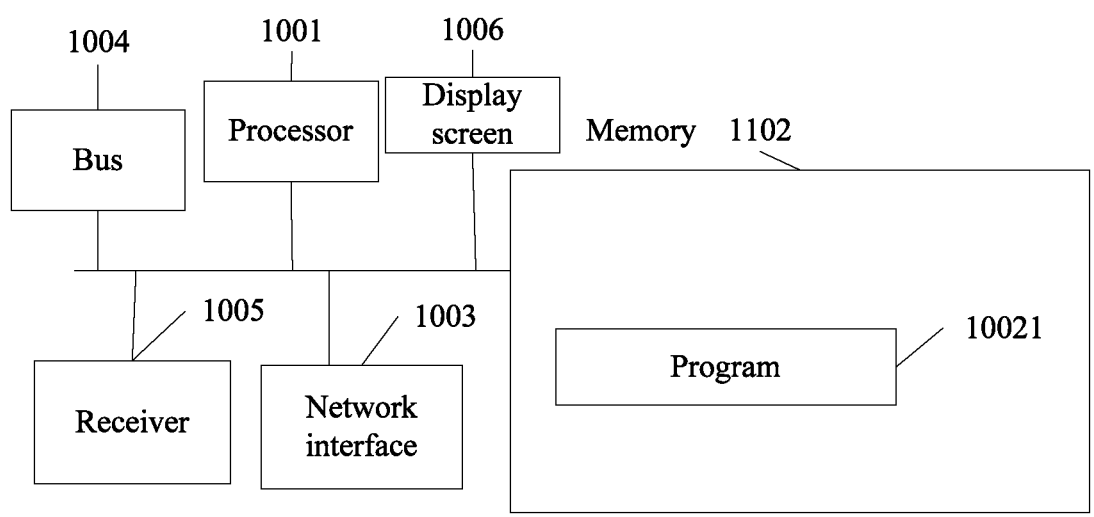
FIG. 11 is a structural diagram of an apparatus for coordinating body devices for communication according to another embodiment of the present invention.

FIG. 11 shows a structure of an apparatus for coordinating body devices for communication provided in another embodiment of the present invention, including at least one processor 1001 (for example, a CPU), a memory 1002, at least one network interface 1003, at least one communications bus 1004, at least one receiver 1005, and a display screen 1006, where the communication bus 1004 is configured to implement connection and communication between these apparatuses. The processor 1001 is configured to execute an executable module, for example, a computer program, stored in the memory 1002. The memory 1002 may include a high-speed random access memory (RAM: Random Access Memory), or may further include a non-volatile memory (non-volatile memory), for example, at least an eMMC (Embedded Multi Media Card, embedded multimedia card) memory. The at least one network interface 1003 (which may be wired or wireless) is configured to implement a communication connection between the network device and at least one other network element, where the Internet, a wide area network, a local area network, a metropolitan area network, or the like may be used. The terminal is configured to execute the method described in the foregoing embodiments.

In some implementation manners, the memory 1002 stores a program 10021, and the program 10021 can be executed by the processor 1001. The program includes:

obtaining an identifier of a body device, and a location parameter and an ambient parameter that are of a user that carries the body device;

obtaining, according to the identifier of the body device, a communication mode supported by the body device;

determining, according to the location parameter and the ambient parameter that are of the user, a scenario situated;

determining a networking mode of the body device according to the scenario and the communication mode supported by the body device; and establishing a connection to the body device according to the networking mode.

Optionally, before the determining a networking mode of the body device according to the scenario and the communication mode supported by the body device, the following is further included:

obtaining a physiological parameter and a behavior parameter that are of the user, where the determining a networking mode of the body device according to the scenario and the communication mode supported by the body device specifically includes:

determining the networking mode of the body device according to the scenario, the communication mode supported by the body device, and the physiological parameter and the behavior parameter that are of the user.

Optionally, after the establishing a connection to the body device according to the networking mode, the following is further included:

determining a network role of the body device according to a network topology, a network optimization algorithm, and the communication mode supported by the body device, where the network role is a local gateway or a terminal; and when the body device is a local gateway, sending an instruction to a terminal within a preset range, so that the terminal within the preset range establishes a connection to the body device, where the preset range is determined according to a direction and a location that are of the body device; or when the body device is a terminal, sending an instruction to the body device, so that the body device establishes a connection to a gateway closest to the body device, where the gateway refers to a local gateway or the mobile personal station, and the mobile personal station determines the gateway closest to the body device according to a location and a direction that are of the body device.

Optionally, after the establishing a connection to the body device according to the networking mode, the following is further included:

monitoring a working status of the body device according to the established connection;

re-determining a network role of the body device according to the network topology when the working status of the body device changes; and performing network optimization according to the network topology and the re-determined network role of the body device.

Optionally, before the establishing a connection to the body device according to the networking mode, the following is further included:

receiving a connection request sent by the body device, where the connection request includes a most power-saving connection mode supported by the body device; and establishing a connection according to the most power-saving connection mode; and the establishing a connection to the body device according to the networking mode specifically includes:

re-establishing a connection to the body device according to the networking mode when the networking mode is different from the most power-saving connection mode.

It can be learned from the foregoing that, the apparatus for coordinating body devices for communication provided in this embodiment of the present invention obtains an identifier of a body device, and a location parameter and an ambient parameter that are of a user that carries the body device; obtains, according to the identifier of the body device, a communication mode supported by the body device; determines, according to the location parameter and the ambient parameter that are of the user, a scenario of the mobile personal station; determines a networking mode of the body device according to the scenario and the communication mode supported by the body device; and establishes a connection to the body device according to the networking mode. A user's scenario and the communication mode supported by the body device are used to determine the networking mode of the body device, which implements communication coordination between body devices and improves user experience.

It should be noted that, to make the description brief, the foregoing method embodiments are expressed as a series of actions. However, a person skilled in the art should appreciate that the present invention is not limited to the described action sequence, because according to the present invention, some steps may be performed in other sequences or performed simultaneously. In addition, a person skilled in the art should also appreciate that all the embodiments described in the specification are exemplary embodiments, and the related actions and modules are not necessarily mandatory to the present invention.

Content such as information exchange and an execution process between the modules in the apparatus and the system is based on a same idea as the method embodiments of the present invention. Therefore, for detailed content, refer to descriptions in the method embodiments of the present invention, and details are not described herein again.

A person of ordinary skill in the art may understand that all or some of the processes of the methods in the embodiments may be implemented by a computer program instructing relevant hardware. The program may be stored in a computer readable storage medium. When the program runs, the processes of the methods in the embodiments are performed. The foregoing storage medium may be a magnetic disk, an optical disc, a read-only memory (Read-Only Memory, ROM), a RAM, or the like.

Specific examples are used in this specification to describe the principle and implementation manners of the present invention. The descriptions of the foregoing embodiments are merely intended to help understand the method and idea of the present invention. In addition, with respect to the implementation manners and the application scope, modifications may be made by a person of ordinary skill in the art according to the idea of the present invention. Therefore, this specification shall not be construed as a limitation on the present invention.

What is claimed is:

1. A method for coordinating body devices for communication, wherein the method comprises:
    obtaining, by a mobile personal station, an identifier of a body device, and a location parameter which includes a parameter of a location of a user that carries the body device, and an ambient parameter which relates to a parameter at the location of the user;
    obtaining, by the mobile personal station according to the identifier of the body device, a communication mode supported by the body device;
    determining, by the mobile personal station according to the location parameter and the ambient parameter that are of the user, a scenario of the user;
    determining, by the mobile personal station, a networking mode of the body device according to the scenario and the communication mode supported by the body device wherein the networking mode designates the communication mode that is used by the body device to connect to the mobile personal station; and
    establishing, by the mobile personal station, a connection to the body device according to the networking mode;
    determining, by the mobile personal station, a network role of the body device according to a network topology, a network optimization algorithm, and the communication mode supported by the body device, wherein the network role is a local gateway or a terminal; and
    sending, by the mobile personal station, one of:
        an instruction to a terminal within a preset range when the body device is a local gateway, so that the terminal within the preset range establishes a connection to the body device, wherein the preset range is determined according to a direction and a location that are of the body device; and
        an instruction to the body device when the body device is a terminal, so that the body device establishes a connection to a gateway closest to the body device, wherein the gateway refers to a local gateway or the mobile personal station, and the mobile personal station determines the gateway closest to the body device according to a location and a direction that are of the body device;
    monitoring, by the mobile personal station, a working status of the body device by using the established connection;
    re-determining, by the mobile personal station, a network role of the body device according to the network topology when the working status of the body device changes; and
    performing, by the mobile personal station, network optimization according to the network topology and the re-determined network role of the body device.

2. The method according to claim 1, before the determining, by the mobile personal station, a networking mode of the body device according to the scenario and the communication mode supported by the body device, further comprising:
    obtaining, by the mobile personal station, a physiological parameter and a behavior parameter that are of the user, wherein
    the determining, by the mobile personal station, a networking mode of the body device according to the scenario and the communication mode supported by the body device specifically comprises:
    determining, by the mobile personal station, the networking mode of the body device according to the scenario, the communication mode supported by the body device, and the physiological parameter and the behavior parameter that are of the user.

3. The method according to claim 1, before the establishing, by the mobile personal station, a connection to the body device according to the networking mode, further comprising:
    receiving, by the mobile personal station, a connection request sent by the body device, wherein the connection request comprises a most power-saving connection mode supported by the body device; and
    establishing, by the mobile personal station, a connection according to the most power-saving connection mode; wherein
    the establishing, by the mobile personal station, a connection to the body device according to the networking mode specifically comprises:
    re-establishing, by the mobile personal station, a connection to the body device according to the networking mode when the networking mode is different from the most power-saving connection mode.

4. An apparatus for coordinating body devices for communication, wherein the apparatus comprises:
    an obtaining unit, configured to obtain an identifier of a body device, and a location parameter which includes a parameter of a location of a user that carries the body device, and an ambient parameter which relates to a parameter at the location of the, wherein
    the obtaining unit is further configured to obtain, according to the identifier of the body device, a communication mode supported by the body device;
    a first determining unit, configured to determine, according to the location parameter and the ambient parameter that are of the user, a scenario of the user, wherein
    the first determining unit is further configured to determine a networking mode of the body device according to the scenario and the communication mode supported by the body device, wherein the networking mode designates the communication mode that is used by the body device to connect to the mobile personal station; and
    a first connection unit, configured to establish a connection to the body device according to the networking mode;
    a receiving unit configured to receive a connection request sent by the body device, wherein the connection request comprises a most power-saving connection mode supported by the body device;

a second connection unit configured to establish a connection according to the most power-saving connection mode; and the first connection unit is configured to re-establish a connection to the body device according to the networking mode when the networking mode is different from the most power-saving connection mode.

5. The apparatus according to claim 4, wherein
the obtaining unit is further configured to obtain a physiological parameter and a behavior parameter that are of the user; and the first determining unit is specifically configured to determine the networking mode of the body device according to the scenario, the communication mode supported by the body device, and the physiological parameter and the behavior parameter that are of the user.

6. The apparatus according to claim 4, wherein after the first connection unit establishes the connection to the body device according to the networking mode, the apparatus further comprises a second determining unit and a sending unit, wherein the second determining unit is configured to determine a network role of the body device according to a network topology, a network optimization algorithm, and the communication mode supported by the body device, wherein the network role is a local gateway or a terminal;

the sending unit is configured to: sends an instruction to a terminal within a preset range when the body device is a local gateway, so that the terminal within the preset range establishes a connection to the body device, wherein the preset range is determined according to a direction and a location that are of the body device; and the sending unit is further configured to: send an instruction to the body device when the body device is a terminal, so that the body device establishes a connection to a gateway closest to the body device, wherein the gateway refers to a local gateway or the mobile personal station, and the mobile personal station determines the gateway closest to the body device according to the location and the direction that are of the body device.

7. The apparatus according to claim 6, wherein the apparatus further comprises: a monitoring unit, a third determining unit, and a network optimization unit, wherein the monitoring unit is configured to monitor a working status of the body device by using the connection established by the first connection unit;

the third determining unit is configured to re-determine a network role of the body device according to the network topology when the working status of the body device changes; and the network optimization unit is configured to perform network optimization according to the network topology and the re-determined network role of the body device.

* * * * *